US012590187B2

(12) United States Patent
Ding et al.

(10) Patent No.: US 12,590,187 B2
(45) Date of Patent: Mar. 31, 2026

(54) POLYMER COMPOSITE CAPABLE OF BEING QUICKLY DISSOLVED OR DISPERSED IN AQUEOUS SOLVENT AND PREPARATION METHOD AND APPLICATION THEREOF

(71) Applicants: Fudan University, Shanghai (CN); Zhuhai Fudan Innovation Institute, Zhuhai (CN)

(72) Inventors: Jiandong Ding, Shanghai (CN); Jingyu Tang, Shanghai (CN); Dinglingge Cao, Shanghai (CN); Lin Yu, Shanghai (CN)

(73) Assignees: Fudan University, Shanghai (CN); Zhuhai Fudan Innovation Institute, Zhuhai (CN)

( * ) Notice: Subject to any disclaimer, the term of this patent is extended or adjusted under 35 U.S.C. 154(b) by 633 days.

(21) Appl. No.: 17/407,160

(22) Filed: Aug. 19, 2021

(65) Prior Publication Data

US 2021/0380764 A1      Dec. 9, 2021

Related U.S. Application Data

(63) Continuation of application No. PCT/CN2020/097939, filed on Jun. 24, 2020.

(30) Foreign Application Priority Data

Mar. 12, 2020    (CN) .......................... 202010171092.5

(51) Int. Cl.
| | |
|---|---|
| *C08G 81/00* | (2006.01) |
| *A61K 8/19* | (2006.01) |
| *A61K 8/27* | (2006.01) |
| *A61K 8/90* | (2006.01) |
| *A61K 47/02* | (2006.01) |
| *A61K 47/34* | (2017.01) |
| *C08K 3/105* | (2018.01) |
| *C08K 3/16* | (2006.01) |
| *C08K 3/30* | (2006.01) |
| *C08K 5/098* | (2006.01) |
| *C08L 71/02* | (2006.01) |
| *C08L 87/00* | (2006.01) |

(52) U.S. Cl.
CPC ................ *C08G 81/00* (2013.01); *A61K 8/19* (2013.01); *A61K 8/27* (2013.01); *A61K 8/90* (2013.01); *A61K 47/02* (2013.01); *A61K 47/34* (2013.01); *C08K 3/105* (2018.01); *C08K 3/16* (2013.01); *C08K 3/30* (2013.01); *C08K 5/098* (2013.01); *C08L 71/02* (2013.01); *C08L 87/005* (2013.01); *C08G 2230/00* (2013.01); *C08K 2003/162* (2013.01); *C08K 2003/3072* (2013.01); *C08K 2201/018* (2013.01)

(58) Field of Classification Search
CPC ........ C08L 71/02; C08L 101/14; C08L 87/00; C08L 87/005; C08L 1/284; C08K 5/098; C08K 3/16; C08K 2003/162; C08K 3/105; A61K 47/10; A61K 47/34
See application file for complete search history.

(56) References Cited

U.S. PATENT DOCUMENTS

| | | | | |
|---|---|---|---|---|
| 2003/0228366 A1* | 12/2003 | Shih | ........................ | A61K 47/14 424/486 |
| 2010/0286075 A1* | 11/2010 | Lee | .......................... | C08L 71/02 514/27 |
| 2013/0345297 A1* | 12/2013 | Lee | ....................... | A61K 31/337 514/449 |

FOREIGN PATENT DOCUMENTS

| | | | | |
|---|---|---|---|---|
| CN | 101229117 A | 7/2008 | | |
| CN | 101229118 A | 7/2008 | | |
| CN | 101273962 A | 10/2008 | | |
| CN | 101273963 A | 10/2008 | | |
| CN | 101273964 A | 10/2008 | | |
| CN | 103622902 A | 3/2014 | | |
| CN | 109675122 A | 4/2019 | | |
| CN | 111286204 A | 6/2020 | | |
| WO | WO-9907343 A1 * | 2/1999 | ............. | A61K 47/34 |

* cited by examiner

*Primary Examiner* — Kregg T Brooks
(74) *Attorney, Agent, or Firm* — Cooper Legal Group, LLC

(57) ABSTRACT

The present application relates to a polymer composite capable of being quickly dissolved or dispersed in an aqueous solvent, and a preparation method and an application thereof. The polymer composite includes a polymer capable of being thermodynamically dissolved in water or an aqueous solvent and a dispersant containing an ion capable of coordinating with the polymer. The polymer is selected from the group of a water soluble homopolymer and/or copolymer, in particular, thermogelable amphiphilic copolymer.

11 Claims, 6 Drawing Sheets

15% PLGA-PEG-PLGA + 1.7% CaCl$_2$

POLYMER COMPOSITE CAPABLE OF BEING QUICKLY DISSOLVED OR DISPERSED IN AQUEOUS SOLVENT AND PREPARATION METHOD AND APPLICATION THEREOF

CROSS-REFERENCE TO RELATED APPLICATION

The application is a continuation of PCT application serial No. PCT/CN2020/097939 filed on Jun. 24, 2020, which claims the priority and benefit to Chinese patent application No. 202010171092.5 filed on Mar. 12, 2020. The entirety of the above-mentioned patent applications is incorporated herein by reference and made a part of this specification.

BACKGROUND

Technical Field

The present application relates to the field of medical polymers, and more specifically, to a polymer composite capable of being quickly dissolved or dispersed in aqueous solvent, and a preparation method and an application thereof.

Description of Related Art

Medical polymers often need to be dissolved in aqueous solvents. However, the dissolution of polymers is usually a very slow process unless treated by long-time stirring, heating, cooling, etc., which obviously limits the application prospects of such polymers.

Taking injectable thermal induced hydrogels as an example, they are a kind of special materials usually formed by dissolving amphiphilic block copolymers in water or other aqueous solvents, which are free flowing micellar solutions at low temperature, and can be changed into a physical gel with temperature rise. The resultant gel could be called a thermogel, and the corresponding copolymer is called a thermogelable polymer. This inverse thermal gelation property gives them wide application prospects in medical and health fields, especially for drug delivery carriers. At low temperatures, the drug can be physically mixed with the solution, and after injection into the body, the thermoinduced gelation can control the release of drugs, which is particularly useful for the treatments of many diseases such as cancer and diabetes. In the prevention of tissue adhesion, gelation of these materials after wound coating can well prevent postoperative tissue adhesion. In endoscopic mucosal dissection surgery, such a thermogel material can be easily injected into the position between the lesion mucosa and the basal tissue through endoscopy, so that the lesion mucosa can be more conveniently stripped after separation from the basal tissue. In addition, such a kind of materials can also play a role of filling and shaping by forming a gel after being injected into the body, and thus can be used for medical cosmetology. The polymers of injectable thermogels are usually polyester-polyether block copolymers, which are easily degradable in water. While biodegradability is very important in medical applications, a polymer susceptible to hydrolysis is not conducive to storage and transportation. However, if the raw material be preserved in a solid state, the dissolution of the bulk polymer in an aqueous solvent is very slow and usually requires more than 12 h of mechanical stirring, which limits their application prospect. So it is much important to develop a polymer composite capable of being dissolved or dispersed quickly in an aqueous solvent and the preparation method thereof.

A China patent application (publication No. CN 109675122 A) discloses an instant thermogel composite consisting of crystallizable solids and block copolymers of poly(ethylene glycol) and biodegradable aliphatic polyester, which is obtained by drying of a mixture of the thermogelable copolymer and a crystallizable material in a solvent such as water or the like. The thermogel composite of that invention can be preserved at a dry state. What is more, the dissolution is not as complicated as the conventional way. For instance, as described in the first paragraph of Summary of the Invention of CN 109675122 A (Paragraph [0005]), "the present application provides a solid composite capable of being dissolved in water under stirring", the rapid dissolution of the instant dissolvable thermogel composite disclosed in that patent is performed with stirring, which still requires the assistance of a special mechanical equipment in practical application, increasing inconvenience for use in a hospital. In addition, the crystallizable solid materials in the composite described in the patent CN 109675122 A are some organic compounds like glucose, which are hard to have a coordination interaction with the polymer molecules. In contrast to it, coordination between our water-soluble polymer and some additives is taken advantage of.

SUMMARY

In view of the above problems in existing technologies, the present application provides a polymer composite which can be quickly dissolved or dispersed in an aqueous solvent by means of coordination between a dispersant and a polymer. The composite can be stored stably, and can be quickly dissolved or dispersed in an aqueous solvent by various ways even including simply shaking in hands. The dispersed solution is injectable and has a property of thermal induced gelation.

In one aspect, the present application provides the following technical solutions:

A polymer composite capable of being quickly dissolved or dispersed in an aqueous solvent, which is compounded from a dispersant containing a coordination ion and a water-soluble polymer, in which the content of the dispersant in the composite is 1-50 wt %, preferably, 10-40 wt %, and the polymer is one or two selected from a group consisting of a water soluble homopolymer and copolymer. In some embodiments, the polymer is an amphiphilic copolymer.

Preferably, the dispersant is selected from calcium salt or combination of calcium salt with one or more selected from the group consisting of citrate, iron salt, zinc salt, magnesium salt, tranexamic acid or 5-aminoketvaleric acid.

Preferably, the calcium salt is one or more selected from a group consisting of calcium lactate, calcium acetate, calcium chloride or calcium hydrogen phosphate, and the citrate is one or more selected from a group consisting of monosodium citrate, disodium citrate, and sodium citrate.

Preferably, a preferred combination of the calcium salt and the citrate is calcium chloride and sodium citrate, in which the molar ratio of calcium chloride to sodium citrate is (0.1-99.9):1.

The water-soluble polymer includes an amphiphilic copolymer.

The amphiphilic copolymer is a block copolymer, including a linear and/or branched n block copolymer formed by covalently bonding hydrophilic block A and hydrophobic block B, in which n is an integer of 2-10. Preferably, the amphiphilic copolymer is an AB diblock copolymer, an ABA or BAB triblock copolymer.

The hydrophilic block is poly (ethylene glycol) and/or a derivative thereof.

The hydrophobic block is usually a polyester, which is one or more selected from a group consisting of poly(lactic acid), poly(lactic-co-glycolic acid), polycaprolactone, poly (caprolactone-co-glycolic acid), poly(lactic acid-co-caprolactone), polyvalerolactone, poly(lactic acid-co-valerolactone), polycarbonate, and poly(caprolactone-co-carbonate).

Part or all of the ends of the block copolymer are connected with a functional group, including any one selected from hydrophilic groups consisting of hydroxyl, amino, carboxyl, imidazolyl, aldehyde group, cyano and nitro group, or any one selected from hydrophobic groups consisting of alkyl group, sterol group, alkoxy group, aromatic group, arylheterocyclic group, amide ester group, halogen atom, trichloromethyl group, ester group and mercapto group.

Preferably, the hydrophobic block of the amphiphilic block copolymer has a molecular weight of 500-3000 and the hydrophilic block has a molecular weight of 500-2000.

The composite can be quickly dissolved or dispersed into an aqueous solvent within 30 minutes by manual shaking to form an injectable solution having a thermally induced gelation performance. Preferably, it can be quickly dissolved or dispersed within 3 minutes by manual shaking. More preferably, it can be quickly dissolved or dispersed within 1 minutes by manual shaking. Further preferably, it can be quickly dissolved or dispersed within 0.5 minutes by manual shaking.

A preparation method of a polymer composite capable of being quickly dissolved or dispersed in an aqueous solvent includes the following steps:

Step (1): compounding a dispersant and a polymer in a common solvent to provide a preliminary composite; and Step (2): drying the preliminary composite obtained in step (1) to obtain a solid composite.

In some embodiments, the drying in step (2) is freeze drying.

In some embodiments, the preparation method includes further blending the solid composite obtained in step (2) with a solid dispersant.

Preferably, the content of the dispersant in the common solvent in step (1) is 0.5-20 wt %, and the content of the polymer in the common solvent is 1-40 wt %. In particular, the common solvent is usually pure water, or an aqueous solvent such as an aqueous solution of a drug and an emulsion of a defoaming agent.

Preferably, in step (1), a temperature for compounding of the dispersant and the polymer in the common solvent is −10 to 50° C., and the compounding time is 0.1-24 h. A method for compounding is one selected from a group consisting of stirring, ultrasound, shaking and standing or a combination thereof.

Preferably, in step (2), for freeze drying, a freezing temperature is −200 to −4° C., a freezing time is 0.1-24 h, and a drying time is 6-96 h. The drying refers to a dehydration of the composite in a freezing state by using vacuum to promote the sublimation of ice.

The composite is applicable to prepare biomaterials for drug delivery carriers, prevention of postoperative tissue adhesion, fluid cushion in endoscopic mucosal dissection, cosmetics, medical cosmetology, dressings, and vaccine adjuvants.

The present application discloses a polymer composite capable of being quickly dissolved or dispersed in an aqueous solvent, a preparation method and application thereof. The prepared composite is a solid capable of being stored stably. The solid can, on demand, be quickly dissolved or dispersed into an injectable micellar solution in water or aqueous solution via convenient ways such as simply manual shaking; and the aqueous solution is subject to thermogelation after being injected into the body. Otherwise if a solid material cannot be rapidly dissolved in water and the copolymer is biodegradable in water, an instantly-useful-in-hospital biomaterial should be in an already-dissolved form and stored at low temperatures. The quickly-dissolved solid composite prepared by the present application eliminates the need of being stored at low temperatures and thus is convenient for transportation and use, which is also much valuable for commercialization.

Compared with existing technologies, the composite according to the present application is a solid material prepared after coordination of polymer and ions in dispersant during the dissolving, freezing and drying process. The interaction between the dispersant and polymer molecules can weaken the cohesion among polymer chains significantly while keeping a solid state after drying. Considering further that ions are themselves easy to be dissolved in an aqueous solvent and the polymer like the thermogelable copolymer is, thermodynamically, soluble or partially soluble in an aqueous solvent, the dry polymer-ion composite can, kinetically, be dissolved or dispersed in an aqueous solvent very rapidly, even probably free of additional mechanical assistance and very convenient for an instant use.

DESCRIPTION OF THE EMBODIMENTS

The present application will be described in details in combination with the drawings and specific examples.

EXAMPLE 1

A polymer composite 80P20CaCl$_2$ capable of being quickly dissolved in aqueous solvent included 1.6 g PLA-PEG-PLA with a molecular weight of 1750-1500-1750 and 0.4 g calcium chloride.

Step (1): magnetically stirring 1.6 g PLA-PEG-PLA with molecular weight of 1750-1500-1750 in water at 4° C. for 24 hours to form a solution with a polymer concentration 20 wt %;

Step (2): dissolving 0.4 g calcium chloride in water to form a calcium chloride solution;

Step (3): adding the calcium chloride solution in step (2) into the polymer solution in step (1), diluting with water to a polymer concentration of 15 wt %, mixing, and standing in a water bath at 37° C. for 2 h to form a gel; and Step (4): freezing the gel obtained in step (3) at −80° C. for 4 h, and then vacuum drying in a freeze dryer for 12 h to obtain the polymer composite capable of being quickly dissolved in an aqueous solvent.

Figure 1:
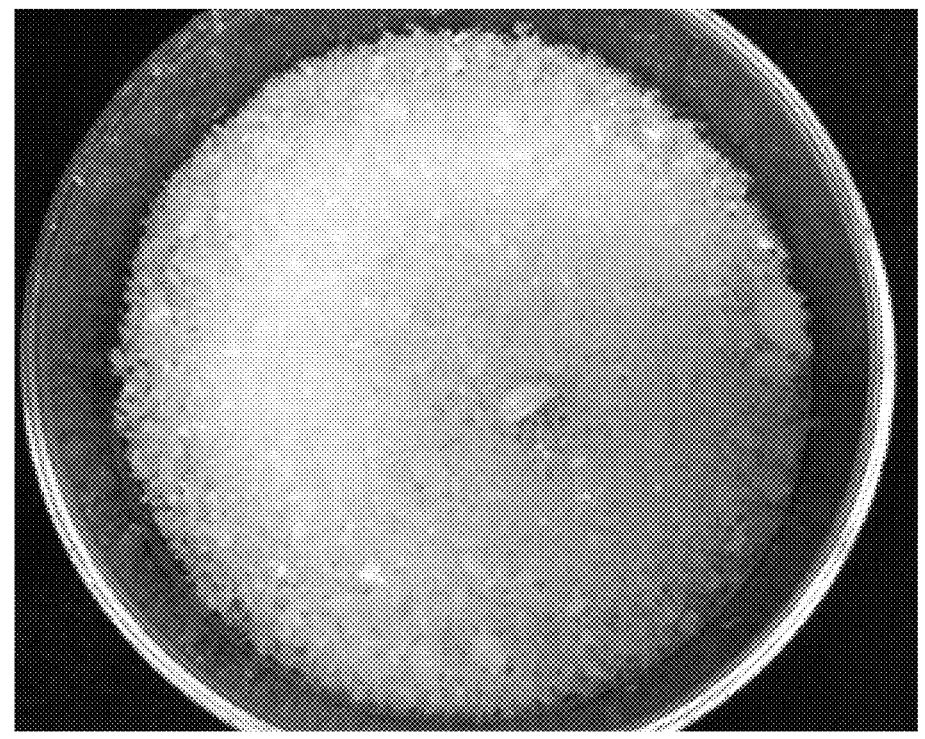
FIG. 1 shows the morphology of composite 80P20CaCl$_2$ in Example 1. Here, "80P20CaCl$_2$" denotes 80 wt % polymer and 20 wt % CaCl$_2$.
Figure 2:
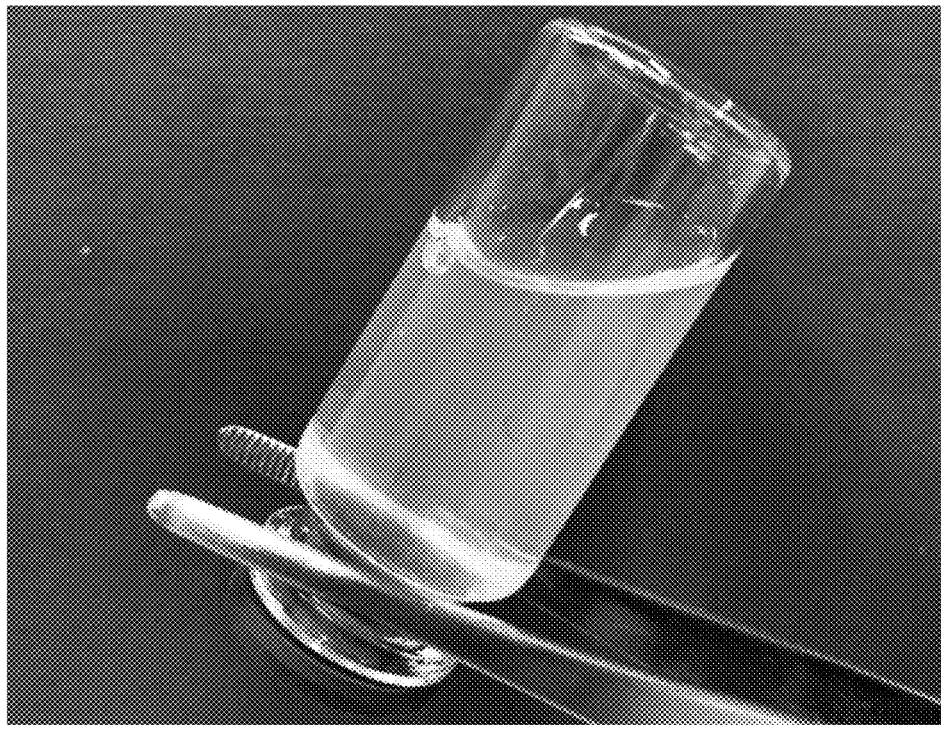
FIG. 2 shows a clear solution of composite 80P20CaCl$_2$ in water formed by shaking in Example 1.
Figure 3:
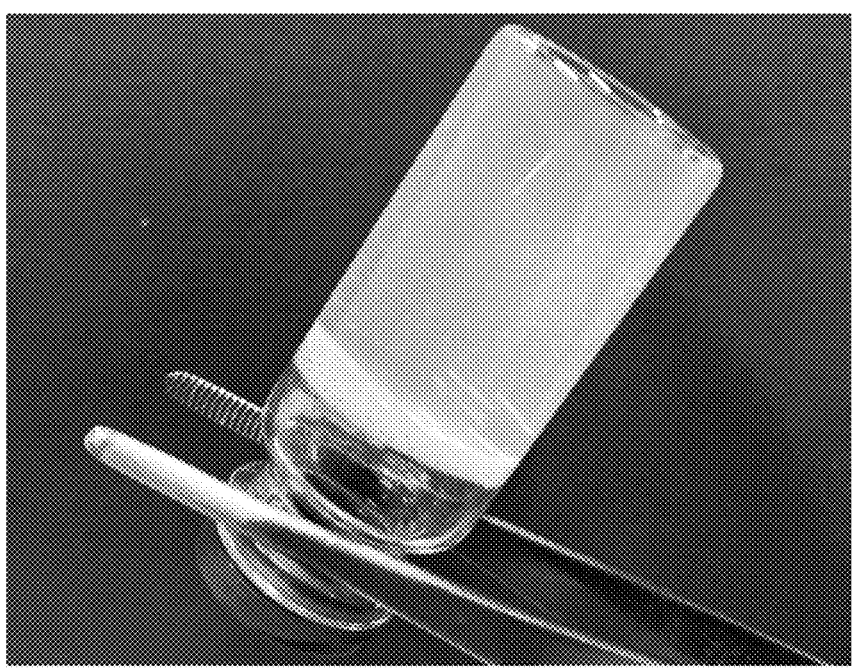
FIG. 3 shows a gel formed at 37° C. from the solution of composite 80P20CaCl$_2$ in water in Example 1.

Characteristics of the polymer composite capable of being quickly dissolving in aqueous solvent are as follow. The solid composite is powder at room temperature (as shown in FIG. 1), and can be dispersed into a clear solution in 10 mL water after manual shaking for 3 minutes (as shown in FIG. 2). The solution is injectable and can be transformed into a gel with the increase of temperature (shown in FIG. 3), with a gelation temperature of 30° C. The injectable hydrogel can be used for drug delivery carriers, prevention of postoperative tissue adhesion, dressings, cosmetics and vaccine adjuvants.

EXAMPLE 2

A polymer composite 90P10CaCl$_2$-1 capable of being quickly dissolved in aqueous solvent included 0.9 g PLGA-PEG-PLGA with a molecular weight of 1500-1000-1500, 0.9 g PLGA-PEG-PLGA with a molecular weight of 1250-1500-1250, and 0.2 g calcium chloride.

Step (1): magnetically stirring the block copolymers with two molecular weights, 0.9 g for each, in water at 4° C. for 24 hours to form a polymer solution with a polymer concentration of 20 wt %;

Step (2): dissolving 0.2 g calcium chloride in water to form a calcium chloride solution;

Step (3): adding the calcium chloride solution in step (2) into the polymer solution in step (1), diluting with water to a polymer concentration of 4.5 wt %, stirring at 20° C. for 0.5 h, raising the temperature to 40° C. under stirring, and stirring for another 0.5 h to provide a composite solution; and Step (4): freezing the solution obtained in step (3) at −20° C. for 12 h, and then vacuum drying in a freeze dryer for 24 h to obtain the polymer composite capable of being quickly dissolved in an aqueous solvent.

The polymer composite capable of being quickly dissolving in aqueous solvent is powdered solid at room temperature, and can be dispersed into a flowable solution in 12 mL water after standing for 30 minutes. The solution is injectable and can be transformed into a gel form with the increase of temperature, with a gelation temperature of 32° C. The gel can be used for drug delivery carriers, prevention of postoperative tissue adhesion, fluid cushion in endoscopic mucosal dissection, and dressings.

EXAMPLE 3

A polymer composite 90P10CaCl$_2$-2 capable of being quickly dissolved in aqueous solvent included 1.8 g PLGA-PEG-PLGA with a molecular weight of 1950-1500-1950 and 0.2 g calcium chloride.

Step (1): magnetically stirring 1.8 g PLGA-PEG-PLGA with molecular weight of 1950-1500-1950 in water at 4° C. for 24 hours to form a polymer solution with a polymer concentration of 20 wt %;

Step (2): dissolving 0.2 g calcium chloride in water to form a calcium chloride solution;

Step (3): adding the calcium chloride solution in step (2) into the polymer solution in step (1), diluting with an aqueous solvent to a polymer concentration of 10 wt %, stirring at 20° C. for 0.5 h, raising the temperature to 40° C. under stirring, and stirring for another 0.5 h to provide a composite solution; and Step (4): freezing the solution obtained in step (3) at −20° C. for 12 h, and then vacuum drying in a freeze dryer for 24 h to obtain the polymer composite capable of being quickly dissolved in an aqueous solvent.

Figure 4:
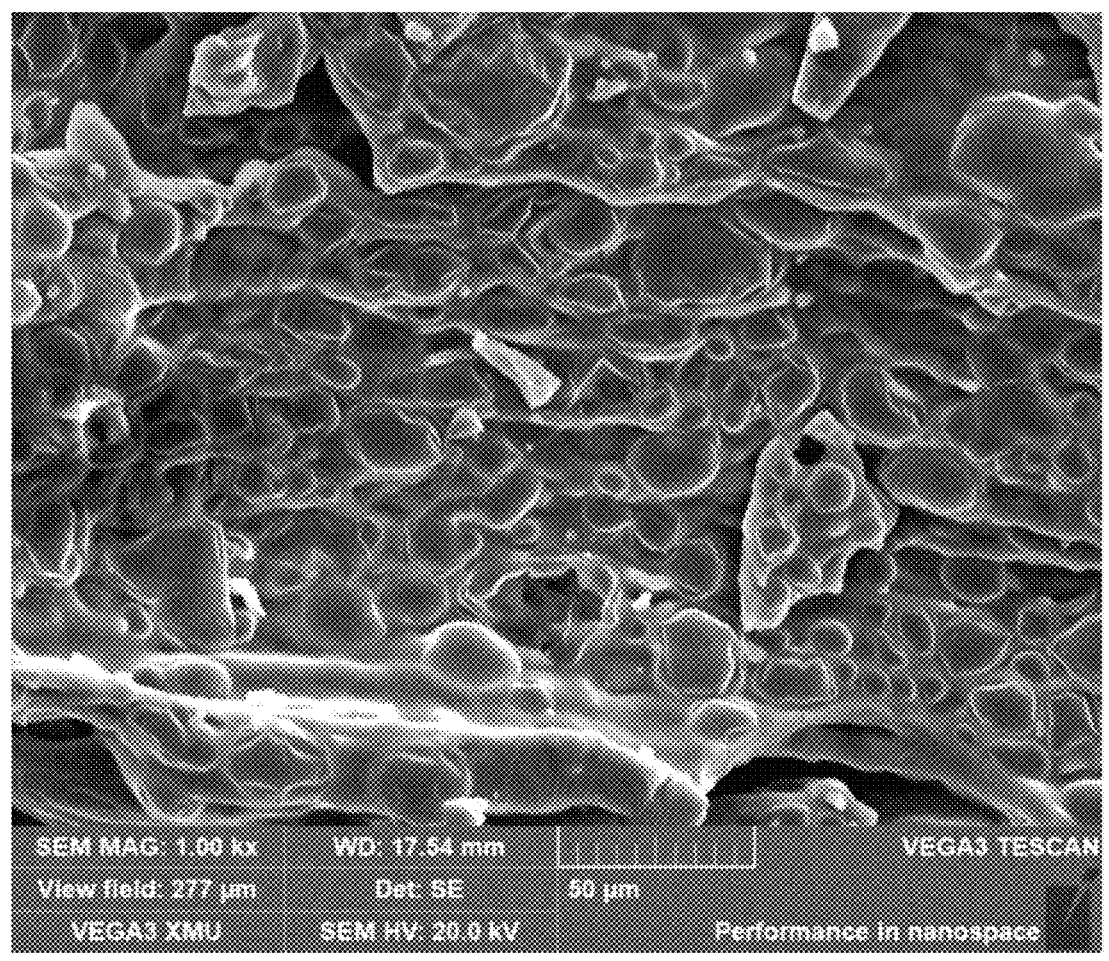
FIG. 4 shows a scanning electron microscopy (SEM) image of composite 90P10CaCl$_2$-2 in Example 3.
Figure 5:
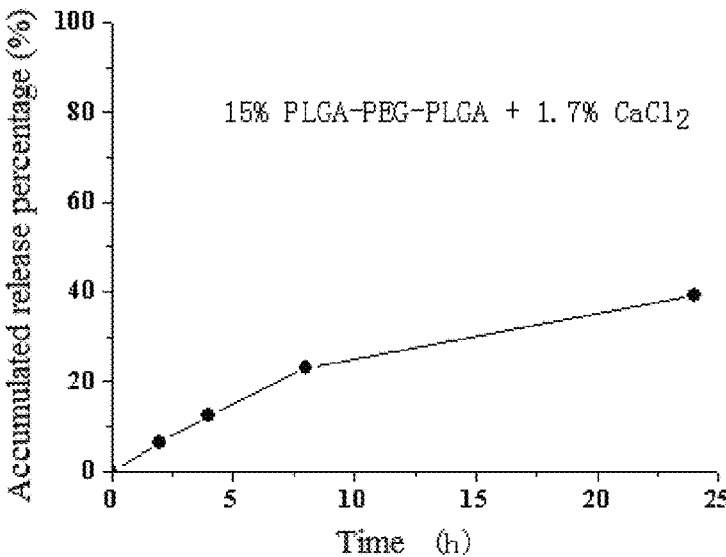
FIG. 5 shows a slow release of calcium ions from the gel formed after dissolution of composite 90P10CaCl$_2$-2 in Example 3.

The polymer composite capable of being quickly dissolved in an aqueous solvent is powdered solid at room temperature exhibiting the micrograph typically presented in FIG. 4, and can be dispersed into a clear solution in 10 mL water after manual shaking for 10 minutes. The solution is injectable and can be transformed into a gel form with the increase of temperature, with a gelation temperature of 34° C. The gel can slowly release calcium ions (as shown in FIG. 5). An accumulated release percentage of calcium ions was 6% at 2 h, corresponding to a calcium ion concentration of 38 mg/L in the solution, which is similar to the calcium ion concentration in tissues of a human body. The gel can be used for drug delivery carriers, prevention of postoperative tissue adhesion, fluid cushion in endoscopic mucosal dissection, and dressings.

EXAMPLE 4

A polymer composite 85P15CaCl$_2$ capable of being quickly dissolved in aqueous solvent included 1.7 g PLGA-PEG-PLGA with a molecular weight of 1950-1500-1950 and 0.3 g calcium chloride.

Step (1): magnetically stirring 1.7 g PLGA-PEG-PLGA with molecular weight of 1950-1500-1950 in water until dissolving to form a solution with a polymer concentration of 20 wt %;

Step (2): dissolving 0.3 g calcium chloride in ethanol to form a solution of calcium chloride in ethanol;

Step (3): adding the solution of calcium chloride in ethanol in step (2) into the polymer solution in step (1), diluting with water and ethanol in which the ethanol had a content of 20 wt % to a polymer concentration of 5 wt %, mixing, and stirring at −10° C. for 2 h; and Step (4): freezing a solution obtained in step (3) at −80° C. for 12 h, and then vacuum drying in a freeze dryer for 24 h to obtain the polymer composite capable of being quickly dissolved in an aqueous solvent.

Figure 6:
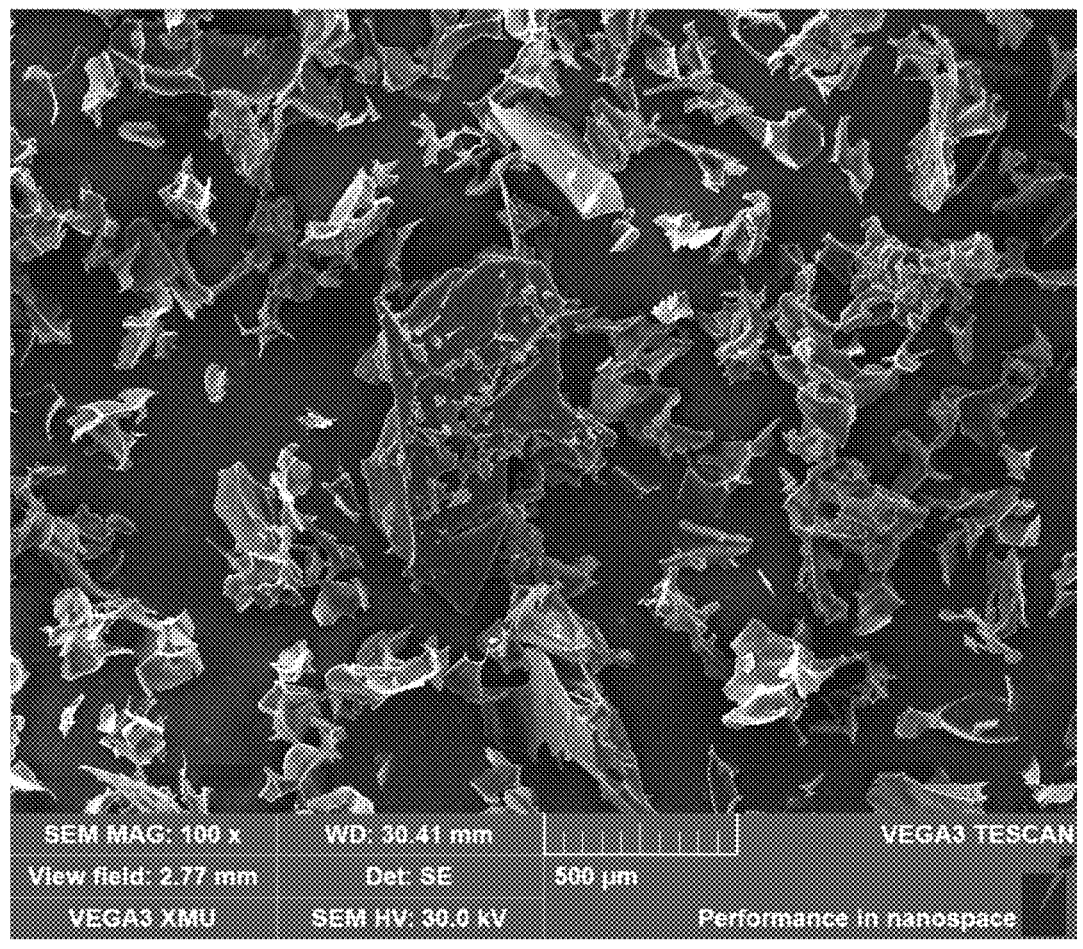
FIG. 6 shows the microscopic morphology (an SEM image) of composite 85P15CaCl$_2$ in Example 4.
Figure 7:
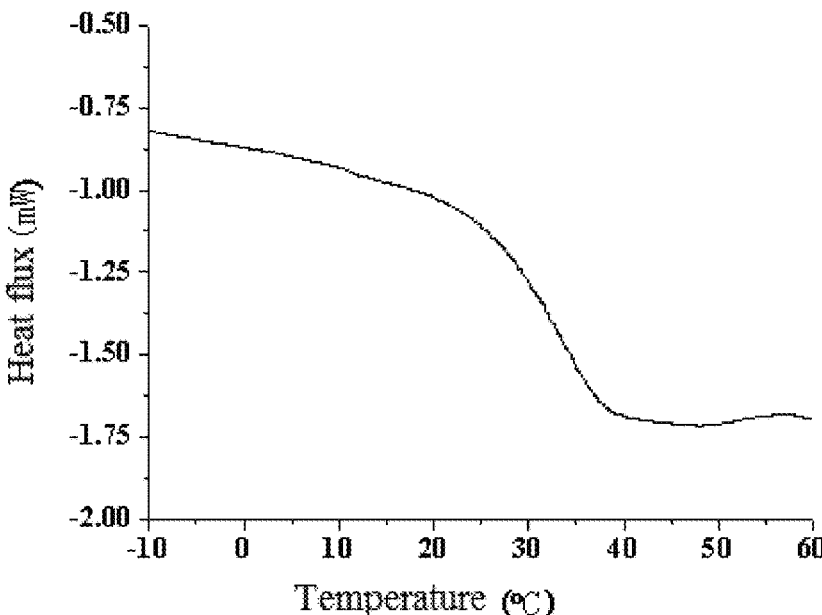
FIG. 7 shows the results of a DSC test of composite 85P15CaCl$_2$ in Example 4.
Figure 8:
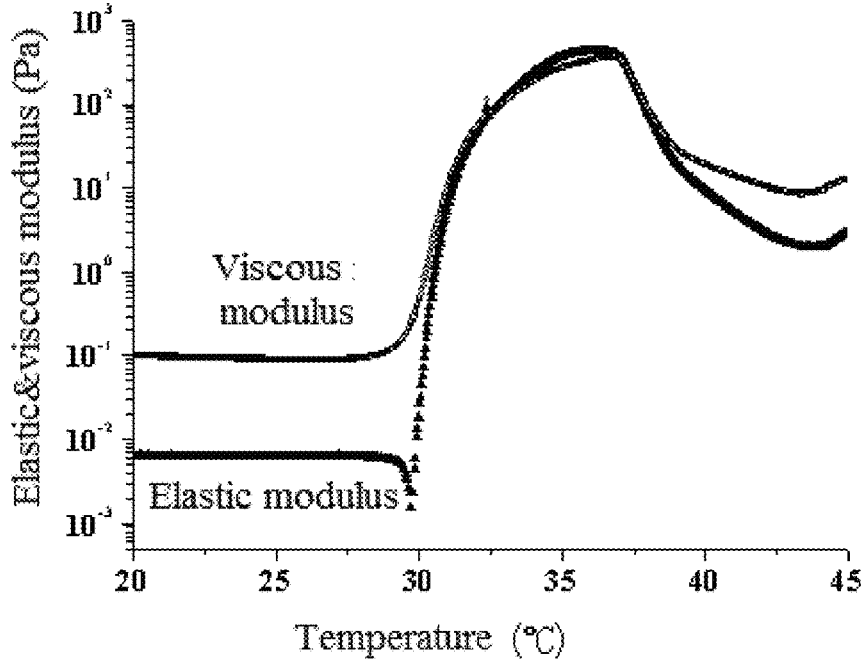
FIG. 8 shows rheological properties of a solution formed after dissolution of composite 85P15CaCl$_2$ in water in Example 4.

The polymer composite capable of being quickly dissolved in an aqueous solvent is powdered solid at room temperature, exhibiting irregular flakes as shown in FIG. 6. DSC tests (FIG. 7) show that the glass transition temperature of the composite is 38.6° C. This transition temperature is beneficial for maintaining the powder form at room temperature. After adding 10 mL of 0.1 M sodium citrate solution at room temperature, the composite can be dispersed into a flowable solution simply by manual shaking for 0.5 min, without the need of a vortex oscillation or magnetic stirring as required in patent CN 109675122 A for dissolving. The rheological tests of the solution (FIG. 8) show that at a temperature below 30° C. the elastic modulus is lower than the viscous modulus, and both of them are less than 0.1 Pa, indicating that the solution is flowable and has good injectable property. With further increase of temperature, the elastic modulus increases and exceeds the viscous modulus, indicating that a sol-to-gel transition occurred, with the gelation temperature being about 32° C. The solution can be injected subcutaneously into an animal to form a gel, without causing obvious adverse reactions, and can be used for drug delivery carrier, prevention of postoperative tissue adhesion, fluid cushion in endoscopic mucosal dissection, and cosmetic or filling agents.

EXAMPLE 5

A polymer composite $90P10Fe_2(SO_4)_3$ capable of being quickly dissolved in aqueous solvent included 1.8 g PLGA-PEG-PLGA with a molecular weight of 1950-1500-1950, 0.19 g ferric sulfate and 0.01 g calcium chloride.

Step (1): magnetically stirring PLGA-PEG-PLGA with a molecular weight of 1950-1500-1950 in water until dissolving to form a polymer solution with a polymer concentration of 15 wt %;

Step (2): dissolving 0.19 g ferric sulfate in water;

Step (3): adding the ferric sulfate solution in step (2) into the polymer solution in step (1), diluting with water to a polymer concentration of 10 wt %, and stirring at room temperature for 0.5 h;

Step (4): spray freeze drying a solution obtained in step (3) to obtain a powdered solid composite; and Step (5): blending the solid composite in step (4) with 0.01 g calcium chloride powder to obtain the polymer composite capable of being quickly dissolved in aqueous solvent.

The polymer composite capable of being quickly dissolving in an aqueous solvent is powdered solid at room temperature, and can be dispersed into a flowable solution by shaking in 10 mL water for 30 min. The solution is injectable, and can be transformed into a gel form with the increase of temperature, with a gelation temperature of 27° C. It can be used as a skin dressing.

EXAMPLE 6

A polymer composite $90P10Zn$ $(CH_3COO)_2$ capable of being quickly dissolved in aqueous solvent included 0.4 g PCGA-PEG-PCGA with a molecular weight of 1800-1500-1800, 1.4 g PLGA-PEG-PLGA with a molecular weight of 1800-1500-1800, 0.15 g zinc acetate, and 0.05 g calcium acetate;

Step (1): magnetically stirring the 0.4 g PCGA-PEG-PCGA and the 1.4 g PLGA-PEG-PLGA together in water until dissolving to form a polymer solution with a polymer concentration of 15 wt %;

Step (2): dissolving 0.15 g zinc acetate and 0.05 g calcium acetate in water;

Step (3): adding a mixture solution obtained in step (2) into the polymer solution in step (1), diluting with water to a polymer concentration of 5 wt %, and stirring at room temperature for 0.5 h; and Step (4): freezing a solution obtained in step (3) at −80° C. for 4 h, and then drying in a freeze dryer for 12 h to obtain the polymer composite capable of being quickly dissolved in an aqueous solvent.

The polymer composite capable of being quickly dissolving in an aqueous solvent is a loose solid at room temperature, and can be dispersed into a flowable solution by shaking in 10 mL water for 30 min. The solution is injectable, and can be transformed into a gel form with the increase of temperature.

EXAMPLE 7

A polymer composite $85P15CaCl_2$-1 capable of being quickly dissolved in aqueous solvent included 1.7 g PCLA-PEG-PCLA with a molecular weight of 1750-1500-1750 and 0.3 g calcium chloride.

Step (1): magnetically stirring 1.7 g PCLA-PEG-PCLA with a molecular weight of 1750-1500-1750 in water at 4° C. for 24 hours to form a polymer solution with a polymer concentration of 20 wt %;

Step (2): dissolving 0.3 g calcium chloride in water to form a calcium chloride solution;

Step (3): adding the calcium chloride solution in step (2) into the polymer solution in step (1), diluting with water to a polymer concentration of 5 wt %, stirring at 20° C. for 0.5 h, raising the temperature to 50° C. under stirring, and stirring for another 0.5 h to provide a composite solution; and Step (4): freezing the solution obtained in step (3) at −20° C. for 12 h, and then vacuum drying in a freeze dryer for 24 h to obtain the polymer composite capable of being quickly dissolved in an aqueous solvent.

The polymer composite capable of being quickly dissolving in an aqueous solvent is powdered solid at room temperature, and can be dispersed into a clear solution in 10 mL water after manual shaking for 1 minute. The solution is injectable and can be transformed into a gel form with the increase of temperature, with a gelation temperature of 34° C. The gel can be used for drug delivery carriers, prevention of postoperative tissue adhesion, fluid cushion in endoscopic mucosal dissection, and dressings.

EXAMPLE 8

A polymer composite $50P40ALA10$ $C_6H_{10}CaO_6$ capable of being quickly dissolved in aqueous solvent included 1 g mPEG-PLGA with a molecular weight of 500-1100, 0.8 g 5-aminolevulinic acid (ALA) and 0.2 g calcium lactate.

Step (1): magnetically stirring 1 g mPEG-PLGA with a molecular weight of 500-1100 in water at 4° C. for 12 h to form a solution with a polymer concentration of 20 wt %;

Step (2): dissolving 0.8 g ALA in the solution in step (1);

Step (3): dissolving 0.2 g calcium chloride in water to form a calcium chloride solution;

Step (4): adding the calcium chloride solution in step (3) into a polymer solution obtained in step (2), diluting with water to a polymer concentration of 5 wt %, mixing, and then performing ultrasonic treatment for 0.1 h; and Step (5): freezing the solution obtained in step (4) at −20° C. for 12 h, and then vacuum drying in a freeze dryer for 30 h to obtain the polymer composite capable of being quickly dissolved in an aqueous solvent.

The polymer composite capable of being quickly dissolved in an aqueous solvent looks like a hard foam at room temperature, and can be dispersed into a clear solution in 3.8 mL water after manual shaking for 5 minutes. The solution can be transformed into a gel form with the increase of temperature, with a gelation temperature of 26° C. The gel can release ALA after forming a gel layer on a skin, and thus can be used for the treatment of acne, condyloma acuminatum and skin cancer.

EXAMPLE 9

A polymer composite 50P40TXA10CaCl₂ capable of being quickly dissolved in aqueous solvent included 0.5 g mPEG-PLGA with a molecular weight of 550-1150, 0.4 g tranexamic acid (TXA) and 0.1 g calcium chloride.

Step (1): dissolving 0.5 g mPEG-PLGA with molecular weight of 550-1150 in 49 g water under stirring at room temperature;

Step (2): adding 0.4 g TXA and 0.1 g calcium chloride into a solution obtained in step (1), and shaking at room temperature for 0.1 h; and Step (3): freezing the solution obtained in step (2) in liquid nitrogen for 0.5 h, and then vacuum drying in a freeze dryer for 30 h to obtain the polymer composite capable of being quickly dissolved in aqueous solvent.

The polymer composite capable of being quickly dissolving in aqueous solvent is a hard solid at room temperature, and can be dispersed into a clear solution in 2 mL water after manual shaking for 5 minutes. The solution can be transformed into a gel form with the increase of temperature, with a gelation temperature of 24° C. The solution can form a gel at a wound to promote coagulation and tissue repair, and can be used as wound dressings.

EXAMPLE 10

A polymer composite 95P5CaCl₂ capable of being quickly dissolved in aqueous solvent included 1.9 g PEG-PLGA-PEG with a molecular weight of 550-2500-550 and 0.1 g calcium chloride.

Step (1): dissolving 1.9 g PEG-PLGA-PEG with a molecular weight of 550-2500-550 in water under stirring at 4° C. for 12 h to form a solution with a polymer concentration of 15 wt %;

Step (2): adding 0.1 g calcium chloride into the solution in step (1), and stirring for another 0.5 h at 4° C. for complete dissolving; and Step (3): standing the solution obtained in step (2) at −4° C. for 24 h, and then vacuum drying in a freeze dryer for 30 h to obtain the polymer composite capable of being quickly dissolved in an aqueous solvent.

The polymer composite capable of being quickly dissolved in an aqueous solvent is a hard solid at room temperature, and can be dispersed into a clear solution in 7.6 mL water after standing at 4° C. for 12 h. The solution can be transformed into a gel form with the increase of temperature, with a gelation temperature of 34° C. The gel can be used for drug delivery carriers, prevention of postoperative tissue adhesion, fluid cushion in endoscopic mucosal dissection, and dressings.

EXAMPLE 11

A polymer composite 90P10C₆H₁₀CaO₆ capable of being quickly dissolved in aqueous solvent included 1.8 g PLGA-PEG-PLGA with a molecular weight of 1750-1500-1750 and 0.2 g calcium lactate.

Step (1): dissolving 1.8 g PLGA-PEG-PLGA with a molecular weight of 1750-1500-1750 in water under stirring at 4° C. for 12 h to form a solution with a polymer concentration of 10 wt %;

Step (2): adding 0.2 g calcium lactate into the solution in step (1), and stirring for another 0.5 h at 4° C. for complete dissolving; and Step (3): freezing the solution obtained in step (2) at −20° C. into ice, and then vacuum drying in a freeze dryer for 24 h to obtain the polymer composite capable of being quickly dissolved in an aqueous solvent.

The polymer composite capable of being quickly dissolved in an aqueous solvent is a loose solid at room temperature, and can be dispersed into a clear solution in 10 mL water under stirring at room temperature for 30 min. The solution can be transformed into a gel form with the increase of temperature, with a gelation temperature of 30° C. The gel can be used for drug delivery carriers, prevention of postoperative tissue adhesion, fluid cushion in endoscopic mucosal dissection, and dressings.

EXAMPLE 12

A polymer composite 90P10MgCl₂ capable of being quickly dissolved in aqueous solvent included 1.6 g PVLA-PEG-PVLA with a molecular weight of 1600-1500-1600, 0.2 g PVL-PEG-PVL with a molecular weight of 1600-1500-1600, 0.1 g magnesium chloride and 0.1 g calcium chloride.

Step (1): dissolving 1.6 g PVLA-PEG-PVLA and 0.2 g PVL-PEG-PVL in water under stirring at 4° C. for 12 h to form a solution having a polymer concentration of 10 wt %;

Step (2): adding 0.1 g magnesium chloride and 0.1 g calcium chloride to the solution in step (1), and stirring for dissolving; and Step (3): freezing the solution obtained in step (2) at −20° C. into ice, and then vacuum drying in a freeze dryer for 24 h to obtain the polymer composite capable of being quickly dissolved in an aqueous solvent.

The polymer composite capable of being quickly dissolved in an aqueous solvent is a loose solid at room temperature, and can be dispersed into a clear solution in 10 mL water under stirring at room temperature for 10 min. The solution can be transformed into a gel form with the increase of temperature, with the gelation temperature of 30° C.

EXAMPLE 13

A polymer composite 90P10Ca(CH₃COO)₂ capable of being quickly dissolved in aqueous solvent included 1.8 g PLGA-PEG-PLGA with a molecular weight of 1400-1000-1400 and 0.2 g calcium acetate.

Step (1): dissolving 1.8 g PLGA-PEG-PLGA with a molecular weight of 1400-1000-1400 in water under stirring at 4° C. for 12 h to form a solution having a polymer concentration of 10 wt %;

Step (2): adding 0.2 g calcium acetate to the solution in step (1), and stirring for dissolving; and Step (3): freezing the solution obtained in step (2) at −80° C. into ice, and then vacuum drying in a freeze dryer for 20 h to obtain the polymer composite capable of being quickly dissolved in an aqueous solvent.

The polymer composite capable of being quickly dissolved in an aqueous solvent is a solid at room temperature, and can be dispersed into a clear solution in 16 mL water under stirring at room temperature for 30 min. The solution can be transformed into a gel form upon heating with the gelation temperature 18° C.

EXAMPLE 14

A polymer composite 90P10Ca(HCO$_3$)$_2$ capable of being quickly dissolved in aqueous solvent included 1.8 g mPEG-PLGA with a molecular weight of 750-2000 and 0.2 g calcium bicarbonate.

Step (1): dissolving 1.8 g mPEG-PLGA with a molecular weight of 750-2000 in water under stirring at 4° C. for 12 h to form a solution having a polymer concentration of 5 wt %;

Step (2): adding 0.2 g calcium bicarbonate to the solution in step (1), and stirring for dissolving; and Step (3): freezing the solution obtained in step (2) at −10° C. into ice, and then vacuum drying in a freeze dryer for 22 h to obtain the polymer composite capable of being quickly dissolved in an aqueous solvent.

The polymer composite capable of being quickly dissolved in an aqueous solvent is a white solid at room temperature, and can be dispersed into a clear solution in 8 mL water under stirring at room temperature for 5 min. The solution can be transformed into a gel upon heating with the gelation temperature of 34° C.

EXAMPLE 15

A polymer composite 50P10CaCl$_2$40ALA capable of being quickly dissolved in an aqueous solvent included 1 g PLGA-PEG-PLGA with a molecular weight of 1850-1500-1850, 0.2 g calcium chloride, and 0.8 g 5-aminolevulinic acid hydrochloride.

Step (1): magnetically stirring 1 g PLGA-PEG-PLGA with a molecular weight of 1850-1500-1850 in water until dissolving to form a solution with a polymer concentration of 20 wt %;

Step (2): dissolving 0.2 g calcium chloride in water;

Step (3): adding a calcium chloride solution obtained in step (2) to the polymer solution obtained in step (1), diluting with water to a polymer concentration of 5 wt %, mixing, and stirring at 50° C. for 0.1 h; and Step (4): freezing the solution obtained in step (3) at −20° C. for 12 h, and then vacuum drying in a freeze dryer for 24 h to obtain a powdered solid; and Step (5): mixing 0.8 g 5-aminolevulinic acid hydrochloride with the powdered solid obtained in step (4) to obtain the polymer composite capable of being quickly dissolved in an aqueous solvent.

The polymer composite capable of being quickly dissolved in an aqueous solvent is a powdered solid at room temperature, and can be dispersed into a flowable solution in 4 mL water by manual shaking for 0.5 minutes. The solution is injectable and can be transformed into a gel upon heating with the sol-gel transition temperature, namely, gelation temperature 30° C.

EXAMPLE 16

A polymer composite 50P50CaCl$_2$ capable of being quickly dissolved in aqueous solvent included 0.45 g PLA-PEG-PLA with a molecular weight of 1850-1500-1850, 0.05 g PLGA-PEG-PLGA with a molecular weight of 500-2000-500, and 0.5 g calcium chloride.

Step (1): magnetically stirring the block copolymers of two molecular weights in 2 g water at 4° C. for 24 h to form a polymer solution;

Step (2): adding 0.5 g calcium chloride into the solution in step (1);

Step (3): stirring a solution obtained in step (2) at 4° C. for 2 h to obtain a composite solution; and Step (4): freezing a solution obtained in step (3) at −200° C. for 0.1 h, and then vacuum drying in a freeze dryer for 6 h to obtain the polymer composite capable of being quickly dissolved in an aqueous solvent to obtain a solid composite.

The polymer composite capable of being quickly dissolved in an aqueous solvent is a solid block at room temperature, and can be dispersed into a flowable solution in 4.5 mL water after manual shaking for 3 minutes. The solution is injectable and can be transformed into a gel with the increase of temperature.

EXAMPLE 17

A polymer composite 90PEG10CaCl$_2$ capable of being quickly dissolved in aqueous solvent included 1.8 g PEG with a molecular weight of 6000 and 0.2 g calcium chloride.

Step (1): magnetically stirring the 1.8 g PEG in 5 g water at room temperature for 24 h to form a polymer solution;

Step (2): adding 0.2 g calcium chloride into the solution in step (1);

Step (3): stirring a solution obtained in step (2) at 25° C. for 0.5 h to obtain a composite solution; and Step (4): freezing a solution obtained in step (3) at −80° C. for 12 h, and then vacuum drying in a freeze dryer for 30 h to obtain the polymer composite capable of being quickly dissolved in an aqueous solvent.

The polymer composite capable of being quickly dissolved in an aqueous solvent is a solid block at room temperature, and can be dispersed into a flowable solution in 5 mL water after manual shaking for 1 minutes. The solution is injectable.

EXAMPLE 18

A polymer composite 80P20CaCl$_2$—C$_6$H$_7$NaO$_7$ capable of being quickly dissolved in aqueous solvent included 1.6 g PLGA-PEG-PLGA with a molecular weight of 1850-1500-1850, 0.2 g calcium chloride, and 0.2 g monosodium citrate.

Step (1): magnetically stirring the 1.6 g PLGA-PEG-PLGA with a molecular weight of 1850-1500-1850 in 10 g water at 4° C. for 24 h to form a polymer solution;

Step (2): adding 0.2 g calcium chloride into the solution in step (1);

Step (3): stirring a solution obtained in step (2) at 25° C. for 1 h to obtain a composite solution;

Step (4): freezing a solution obtained in step (3) at −80° C. for 12 h, and vacuum drying in a freeze dryer for 30 h to obtain a powdered solid; and Step (5): blending the powdered solid in step (4) with 0.2 g monosodium citrate to obtain the polymer composite capable of being quickly dissolved in an aqueous solvent.

The polymer composite capable of being quickly dissolved in an aqueous solvent is a powder at room temperature, and can be dispersed into a flowable solution by manual shaking in 10 mL water for 1 min. The solution is injectable, and can be transformed into a gel form with the increase of temperature over 33° C.

EXAMPLE 19

A polymer composite 80P20CaCl$_2$—C$_6$H$_6$Na$_2$O$_7$ capable of being quickly dissolved in aqueous solvent included 1.6 g P(CL-co-TMC)-PEG-P(CL-co-TMC) with a molecular weight of 1350-1000-1350, 0.3 g calcium chloride, and 0.1 g disodium citrate.

Step (1): magnetically stirring the 1.6 g P(CL-co-TMC)-PEG-P(CL-co-TMC) in 10 g water at 4° C. for 24 h to form a polymer solution;

Step (2): adding 0.3 g calcium chloride into the polymer solution in step (1);

Step (3): stirring a solution obtained in step (2) at 25° C. for 1 h to obtain a composite solution;

Step (4): freezing a solution obtained in step (3) at −80° C. for 12 h, and then vacuum drying in a freeze dryer for 30 h to obtain a powdered solid; and Step (5): blending the powdered solid in the step (4) with 0.1 g disodium citrate to obtain the polymer composite capable of being quickly dissolved in an aqueous solvent.

The polymer composite capable of being quickly dissolved in an aqueous solvent is a powder at room temperature, and can be dispersed into a flowable solution by manual shaking in 10 mL water for 1 min. The solution is injectable, and can be transformed into a gel form with the increase of temperature over 31° C.

EXAMPLE 20

A polymer composite 80P20CaCl$_2$—C$_6$H$_5$Na$_3$O$_7$-1 capable of being quickly dissolved in aqueous solvent included 1.55 g mPEG-PTMC with a molecular weight of 550-2700, 0.05 g mPEG-PCL with a molecular weight of 750-3000, 0.385 g calcium chloride, and 0.015 g sodium citrate.

Step (1): magnetically stirring the 1.55 g mPEG-PTMC with a molecular weight of 550-2700 and 0.05 g mPEG-PCL with a molecular weight of 750-3000 together in 10 g water at 4° C. for 24 h to form a polymer solution;

Step (2): adding 0.385 g calcium chloride and 0.015 g sodium citrate into the solution in step (1);

Step (3): stirring a solution obtained in step (2) at 25° C. for 1 h to obtain a composite solution; and Step (4): freezing a solution obtained in step (3) at −80° C. for 12 h, and vacuum drying in a freeze dryer for 6 h to obtain a powdered composite.

The polymer composite capable of being quickly dissolved in an aqueous solvent is a powder at room temperature, and can be dispersed into a flowable solution by manual shaking in 10 mL water for 1 min. The solution is injectable, and can be transformed into a gel form with the increase of temperature over 35° C.

EXAMPLE 21

A polymer composite 80P20CaCl$_2$—C$_6$H$_5$Na$_3$O$_7$-2 capable of being quickly dissolved in aqueous solvent included 1.6 g PLGA-PEG-PLGA with a molecular weight of 1850-1500-1850, 0.01 g calcium chloride, and 0.39 g sodium citrate.

Step (1): magnetically stirring the 1.6 g PLGA-PEG-PLGA with a molecular weight of 1850-1500-1850 in 10 g water at 4° C. for 24 h to form a polymer solution;

Step (2): adding 0.01 g calcium chloride, and 0.39 g sodium citrate into the solution in step (1);

Step (3): stirring a solution obtained in step (2) at 25° C. for 1 h, performing ultrasonic treatment for 5 min, and standing for 2 h to obtain a composite solution; and Step (4): freezing a solution obtained in step (3) at −80° C. for 12 h, and vacuum drying in a freeze dryer for 30 h to obtain a powdered composite.

The polymer composite capable of being quickly dissolved in an aqueous solvent is a powder at room temperature, and can be dispersed into a flowable solution by stirring in 10 mL water for 30 min. The solution is injectable, and can be transformed into a gel form with the increase of temperature over 26° C.

EXAMPLE 22

A polymer composite 80P20CaCl$_2$—C$_6$H$_5$Na$_3$O$_7$-3 capable of being quickly dissolved in aqueous solvent included 1.6 g PLGA-PEG-PLGA with a molecular weight of 1850-1500-1850, 0.15 g calcium chloride, 0.05 g calcium lactate, and 0.2 g sodium citrate.

Step (1): magnetically stirring the 1.6 g PLGA-PEG-PLGA with a molecular weight of 1850-1500-1850 in 10 g water at 4° C. for 24 h to form a polymer solution;

Step (2): adding 0.15 g calcium chloride and 0.05 g calcium lactate into the solution in step (1);

Step (3): stirring a solution obtained in step (2) at 25° C. for 1 h to obtain a composite solution;

Step (4): freezing a solution obtained in step (3) at −80° C. for 12 h, and vacuum drying in a freeze dryer for 30 h to obtain a powdered solid; and Step (5): blending the powdered solid in step (4) with 0.2 g sodium citrate to obtain the polymer composite capable of being quickly dissolved in an aqueous solvent.

Characteristics of the polymer composite capable of being quickly dissolved in an aqueous solvent are as follow: it is a powder at room temperature, and can be dispersed into a flowable solution by manual shaking in 10 mL water for 0.5 min; the solution is injectable, and can be transformed into a gel form with the increase of temperature; the gelation temperature of 30° C. The gel can be used for drug delivery carriers, prevention of tissue adhesion, cosmetics, medical cosmetology, fluid cushion in endoscopic mucosal dissection, dressings, and vaccine adjuvant.

EXAMPLE 23

A polymer composite 80P20CaCl$_2$—C$_6$H$_5$Na$_3$O$_7$-4 capable of being quickly dissolved in aqueous solvent included 1.6 g mPEG-PLGA with a molecular weight of 550-1150, 0.2 g calcium chloride, and 0.2 g sodium citrate.

Step (1): magnetically stirring the 1.6 g mPEG-PLGA in 20 g water at 4° C. for 24 h to form a polymer solution;

Step (2): adding 0.2 g calcium chloride, and 0.2 g sodium citrate into the solution in step (1);

Step (3): stirring a solution obtained in step (2) at 4° C. for 0.1 h to obtain a composite solution; and Step (4): freezing a solution obtained in step (3) at −80° C. for 12 h, and then vacuum drying in a freeze dryer for 60 h to obtain a powdered composite.

Figure 9:
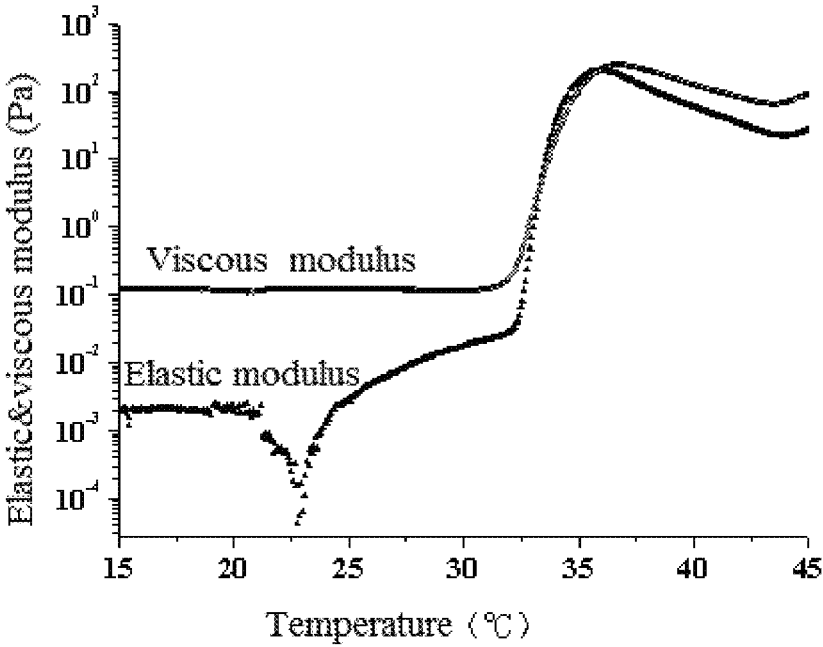
FIG. 9 shows rheological properties of the solution obtained from rapid dissolution of 80P20CaCl$_2$—C$_6$H$_5$Na$_3$O$_7$-4 in Example 23.

Characteristics of the polymer composite capable of being quickly dissolved in an aqueous solvent are as follow. It is a solid powder at room temperature, and can be dispersed into a flowable solution by manual shaking in 9 mL water for 1 min. The solution is injectable, having a property of thermal-responsive gelation. As shown in the rheological measurement in FIG. 9, the gelation temperature read 33° C. The gel can be used for drug delivery carriers, prevention of tissue adhesion, cosmetics, medical cosmetology, fluid cushion in endoscopic mucosal dissection, dressings, and vaccine adjuvant.

EXAMPLE 24

A polymer composite 85P15CaCl$_2$—SC capable of being quickly dissolved in aqueous solvent included 0.7 g PLA-PEG-PLA with a molecular weight of 1500-1000-1500, 1.0 g PLGA-PEG-PLGA with a molecular weight of 1250-1500-1250, 0.2 g calcium chloride, 0.05 g sodium citrate, 0.03 g monosodium citrate, and 0.02 g disodium citrate.
   Step (1): magnetically stirring 0.7 g PLA-PEG-PLA and 1.0 g PLGA-PEG-PLGA in 10 g water at 4° C. for 24 h to form a polymer solution;
   Step (2): adding 0.2 g calcium chloride into the solution in step (1);
   Step (3): stirring a solution obtained in step (2) at 4° C. for 0.5 h to obtain a composite solution;
   Step (4): freezing the composite solution in step (3) at −80° C. for 4 h, and vacuum drying in a freeze dryer for 24 h to obtain a powdered solid; and
   Step (5): blending the powdered solid in step (4) with 0.05 g sodium citrate, 0.03 g monosodium citrate, and 0.02 g disodium citrate to obtain the polymer composite capable of being quickly dissolved in an aqueous solvent.
Characteristics of the polymer composite capable of being quickly dissolved in an aqueous solvent are as follow. It is a powder at room temperature, and can be dispersed into a flowable solution by manual shaking in 10 mL water for 2 min. The solution is injectable, and can be transformed into a gel form with the increase of temperature over 32° C.

EXAMPLE 25

Figure 10:
FIG. 10 shows the morphology of composite 85P15CaCl$_2$—C$_6$H$_5$Na$_3$O$_7$ in Example 25.
Figure 11:
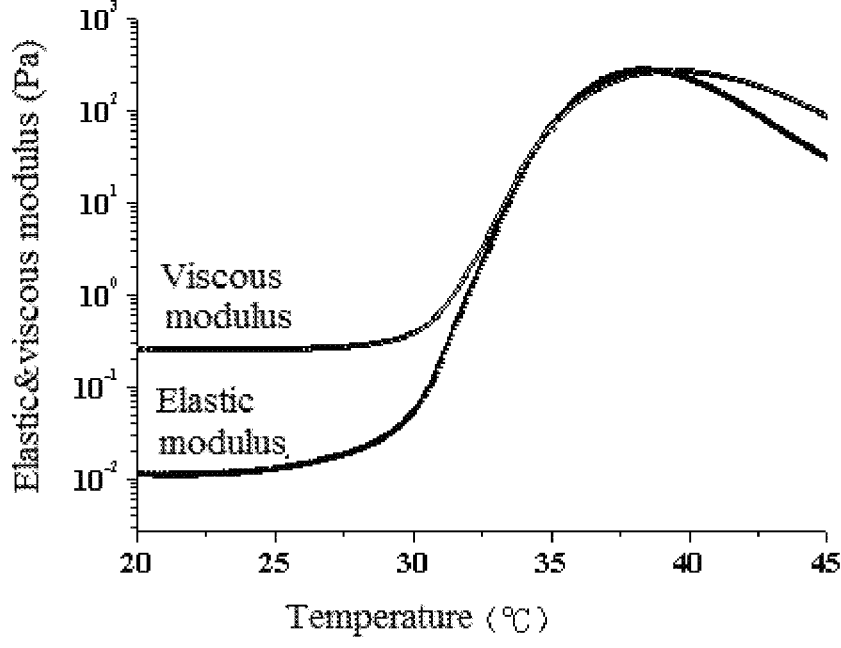
FIG. 11 shows rheological properties of a solution formed by instant dissolution of composite 85P15CaCl$_2$—C$_6$H$_5$Na$_3$O$_7$ in Example 25.

A polymer composite 85P15CaCl$_2$—C$_6$H$_5$Na$_3$O$_7$ capable of being quickly dissolved in aqueous solvent included 1.7 g PLGA-PEG-PLGA with a molecular weight of 1950-1500-1950, 0.2 g calcium chloride, and 0.1 g sodium citrate.
   Step (1): magnetically stirring the 1.7 g PLGA-PEG-PLGA with a molecular weight of 1950-1500-1950 in 10 g water at 4° C. for 24 h to form a polymer solution;
   Step (2): adding 0.2 g calcium chloride into the solution in step (1);
   Step (3): stirring a solution obtained in step (2) at 4° C. for 0.1 h to obtain a composite solution;
   Step (4): freezing a solution obtained in step (3) at −20° C. for 10 h, and then vacuum drying in a freeze dryer for 20 h to obtain a powdered solid; and
   Step (5): blending the powdered solid in step (4) with 0.1 g sodium citrate to obtain the polymer composite capable of being quickly dissolved in an aqueous solvent.
Characteristics of the polymer composite capable of being quickly dissolved in an aqueous solvent are as follow. It is a powder at room temperature, as shown in FIG. 10. The solid can be dispersed into a flowable solution by manual shaking in 15 mL water for 0.5 min. The solution is injectable, having a property of thermal-responsive gelation, with a typical rheological property shown in FIG. 11. The gel can be used for drug delivery carriers, prevention of tissue adhesion, cosmetics, medical cosmetology, fluid cushion in endoscopic mucosal dissection, dressings, and vaccine adjuvant.

EXAMPLE 26

A polymer composite 85P15CaCl$_2$—C$_6$H$_5$Na$_3$O$_7$-1 capable of being quickly dissolved in aqueous solvent included 1.6 g PLGA-PEG-PLGA with a molecular weight of 1950-1500-1950, 0.1 g PCLA-PEG-PCLA with a molecular weight of 1250-1500-1250, 0.2 g calcium chloride and 0.1 g sodium citrate.
   Step (1): magnetically stirring 1.6 g PLGA-PEG-PLGA and 0.1 g PCLA-PEG-PCLA in water until dissolving to form a polymer solution with a polymer concentration of 20 wt %;
   Step (2): adding 0.3 g calcium chloride into ethanol to form a solution of calcium chloride in ethanol;
   Step (3): adding the solution of calcium chloride in ethanol in step (2) to the polymer solution in step (1), diluting with water and ethanol, in which the ethanol content is 20 wt %, until the calcium chloride concentration is 0.5 wt %, mixing by shaking, and then stirring at −10° C. for 24 h;
   Step (4): freezing a solution obtained in step (3) at −80° C. for 4 h, and vacuum drying in a freeze dryer for 96 h to obtain a solid powder; and
   Step (5): blending the solid powder in step (4) with 0.1 g sodium citrate to obtain the polymer composite capable of being quickly dissolved in an aqueous solvent.
Characteristics of the polymer composite capable of being quickly dissolved in an aqueous solvent are as follow. It is a powder at room temperature, and can be dispersed into a flowable solution by manual shaking in 10 mL water for 3 min. The solution is injectable, and can be transformed into a gel form with the increase of temperature.

EXAMPLE 27

A polymer composite 90P10CaCl$_2$—C$_6$H$_5$Na$_3$O$_7$ capable of being quickly dissolved in aqueous solvent included 0.4 g PCGA-PEG-PCGA with a molecular weight of 1800-1500-1800, 1.4 g PLGA-PEG-PLGA with a molecular weight of 1800-1500-1800, 0.15 g calcium chloride, and 0.05 g sodium citrate.
   Step (1): stirring 0.4 g PCGA-PEG-PCGA and 1.4 g PLGA-PEG-PLGA together in water until dissolving to form a polymer solution with a polymer concentration of 10 wt %;
   Step (2): adding 0.15 g calcium chloride and 0.05 g sodium citrate to the polymer solution in step (1), diluting with water until the polymer concentration was 5 wt %, and stirring at room temperature for 0.5 h; and
   Step (3): freezing a solution obtained in step (2) at −200° C. for 0.1 h, and then vacuum drying in a freeze dryer for 18 h to obtain the polymer composite capable of being quickly dissolved in an aqueous solvent.
Characteristics of the polymer composite capable of being quickly dissolved in an aqueous solvent are as follow. It is a loose solid at room temperature, and can be dispersed into a flowable solution by shaking in 10 mL water for 10 min. The solution is injectable, and can be transformed into a gel form with the increase of temperature.

EXAMPLE 28

A polymer composite 50P50CaCl$_2$—C$_6$H$_5$Na$_3$O$_7$ capable of being quickly dissolved in aqueous solvent included 0.45 g PLA-PEG-PLA with a molecular weight of 1850-1500-1850, 0.05 g PLGA-PEG-PLGA with a molecular weight of 500-2000-500, 0.4 g calcium chloride, and 0.1 g sodium citrate.
   Step (1): magnetically stirring the block copolymers with the two molecular weights together in 49.1 g water at 4° C. for 24 h to form a polymer solution;

Step (2): adding 0.4 g calcium chloride into the solution in step (1);

Step (3): stirring a solution obtained in step (2) at 50° C. for 0.1 h to obtain a composite solution;

Step (4): freezing the composite solution in step (3) at −4° C. for 24 h, and vacuum drying in a freeze dryer for 96 h to obtain a powdered composite; and Step (5): blending the powdered solid in step (4) with 0.1 g sodium citrate to obtain the polymer composite capable of being quickly dissolved in an aqueous solvent.

Characteristics of the polymer composite capable of being quickly dissolved in an aqueous solvent are as follow. It is a powdered solid at room temperature, and can be dispersed into a flowable solution by manual shaking in 5 mL water for 3 min. The solution is injectable, and can be transformed into a gel with the increase of temperature.

EXAMPLE 29

A polymer composite $50PEG50CaCl_2$—$C_6H_5Na_3O_7$ capable of being quickly dissolved in aqueous solvent included 2 g PEG with a molecular weight of 3000, 1 g calcium chloride, and 1 g sodium citrate.

Step (1): magnetically stirring 2 g PEG in 2 g water at room temperature for 4 h to form a polymer solution;

Step (2): adding 1 g calcium chloride into the polymer solution in step (1);

Step (3): stirring a solution obtained in step (2) at 25° C. for 0.5 h to obtain a composite solution;

Step (4): freezing a solution obtained in step (3) at −80° C. for 12 h, and vacuum drying in a freeze dryer for 6 h to obtain a solid composite; and Step (5): pulverizing the solid composite in step (4) into powder and blending with 1 g sodium citrate to obtain the polymer composite capable of being quickly dissolved in an aqueous solvent.

Characteristics of the polymer composite capable of being quickly dissolved in an aqueous solvent are as follow. It is a block solid at room temperature, and can be dispersed into a flowable solution by manual shaking in 10 mL water for 1 min.

EXAMPLE 30

A polymer composite $99F1CaCl_2$—$C_6H_5Na_3O_7$ capable of being quickly dissolved in aqueous solvent included 4.95 g Poloxamer F127, 0.025 g calcium chloride, and 0.025 g sodium citrate.

Step (1): magnetically stirring 4.95 g Poloxamer F127 in 10 g water at 4° C. for 24 h to form a polymer solution;

Step (2): adding 0.025 g calcium chloride and 0.025 g sodium citrate into the polymer solution in step (1);

Step (3): stirring a solution obtained in step (2) at 10° C. for 0.1 h to obtain a composite solution; and Step (4): freezing a solution obtained in step (3) at −80° C. for 12 h, and vacuum drying in a freeze dryer for 96 h to obtain a solid composite.

Characteristics of the polymer composite capable of being quickly dissolved in an aqueous solvent are as follow. It is a solid at room temperature, and can be dispersed into a flowable solution by stirring in 20 mL water for 5 min. The solution is injectable, and can be transformed into a gel form with the increase of temperature over 26° C.

EXAMPLE 31

A polymer composite 80P20Ca—SC capable of being quickly dissolved in aqueous solvent included 1.5 g PVLA-PEG-PVLA with a molecular weight of 1600-1500-1600, 0.1 g PVL-PEG-PVL with a molecular weight of 1600-1500-1600, 0.05 g calcium lactate, 0.05 g calcium acetate, 0.05 g calcium hydrogen phosphate, 0.05 g calcium chloride, and 0.2 g sodium citrate.

Step (1): stirring 1.5 g PVLA-PEG-PVLA and 0.1 g PVL-PEG-PVL in water at 4° C. for 12 h to form a polymer solution with a polymer concentration of 10 wt %;

Step (2): adding 0.05 g calcium lactate, 0.05 g calcium acetate, 0.05 g calcium hydrogen phosphate, and 0.05 g calcium chloride into the solution in step (1), and stirring until dissolving;

Step (3): freezing a solution obtained in step (2) at −80° C. into ice, and then vacuum drying in a freeze dryer for 24 h to obtain a powdered composite; and Step (4): blending the powdered composite in step (3) with 0.2 g sodium citrate to obtain the polymer composite capable of being quickly dissolved in an aqueous solvent.

Characteristics of the polymer composite capable of being quickly dissolved in an aqueous solvent are as follow. It is a powder at room temperature, and can be dispersed into a clear solution by stirring in 10 mL water at room temperature for 10 min. The solution can be transformed into a gel form with the increase of temperature.

EXAMPLE 32

A polymer composite 80P20Ca—SC-1 capable of being quickly dissolved in aqueous solvent included 0.01 g branched 4arm-PEG-PLGA (4s-PEG-PLGA) with a molecular weight of 4s-1500-1250, 0.01 g ten-block copolymer $mPEG-(PLGA-PEG)_4$-PLGA with a molecular weight of $750-(1250-1500)_4-1250$, 1.58 g triblock copolymer PLGA-PEG-PLGA with a molecular weight of 1750-1500-1750, 0.2 g calcium lactate, and 0.2 g sodium citrate.

Step (1): stirring 1.58 g PLGA-PEG-PLGA, 0.01 g 4s-PEG-PLGA, and 0.01 g $mPEG-(PLGA-PEG)_4$-PLGA together in water at 4° C. until dissolving to form a polymer solution with a polymer concentration of 5 wt %;

Step (2): adding 0.2 g calcium chloride into the polymer solution in step (1), and stirring at room temperature for 0.5 h;

Step (3): freezing a solution obtained in step (2) at −80° C. into ice, and then vacuum drying in a freeze dryer for 30 h to obtain a powdered composite; and Step (4): blending the powdered composite in step (3) with 0.2 g sodium citrate to obtain the polymer composite capable of being quickly dissolved in an aqueous solvent.

Characteristics of the polymer composite capable of being quickly dissolved in an aqueous solvent are as follow. It is a powder at room temperature, and can form a solution by manual shaking in 10 mL water for 1 min. The solution can be transformed into a gel form with the increase of temperature.

EXAMPLE 33

A polymer composite 80P20Ca—SC-2 capable of being quickly dispersed in aqueous solvent included 1.6 g PCL-PEG-PCL with a molecular weight of 900-1000-900, 0.2 g calcium chloride, and 0.2 g sodium citrate.

Step (1): stirring 1.6 g PCL-PEG-PCL and 0.2 g calcium chloride in water at 80° C. for 5 min, immediately transferring to a water bath at 4° C., and stirring for another 5 min to form a polymer solution with a polymer concentration of 2 wt %;

Step (2): freezing the polymer solution obtained in step (1) at –80° C. into ice, and vacuum drying in a freeze dryer for 30 h to obtain a loose composite; and Step (3): blending the loose composite in step (2) with 0.2 g sodium citrate to obtain the polymer composite capable of being quickly dispersed in an aqueous solvent.

Characteristics of the polymer composite capable of being quickly dispersed in an aqueous solvent are as follow. It is a loose solid at room temperature, and can be dispersed into a suspension liquid by manual shaking in 10 mL water for 1 min. The suspension can be transformed into a gel form with the increase of temperature.

The above description of the embodiment is for the convenience of ordinary technicians in the technical field to understand and use the invention. It is obvious that those skilled in the art can easily make various modifications to these embodiments and apply the general principles described herein to other embodiments without paying creative labor. Therefore, the invention is not limited to the above embodiments. According to the disclosure of the present application, the improvements and modifications made by those skilled in the art without departing from the scope of the invention should be within the protection scope of the present application.

What is claimed is:

1. A polymer composite as a solid capable of being quickly dissolved or dispersed in an aqueous solvent, consisting of:

(1) a polymer which is thermodynamically dissolvable in water or an aqueous solution; and (2) a dispersant containing an ion capable of coordinating with the polymer, wherein the polymer is one or two selected from the group consisting of a water soluble homopolymer and copolymer;

wherein the polymer composite is a solid material after being prepared by coordination of the polymer and the ion in the dispersant, and wherein the polymer composite is capable of being dispersed in water or an aqueous medium to form an injectable solution having a thermally induced gelation property.

2. The polymer composite as a solid capable of being quickly dissolved or dispersed in an aqueous solvent according to claim 1, wherein the polymer is an amphiphilic copolymer.

3. The polymer composite as a solid capable of being quickly dissolved or dispersed in an aqueous solvent according to claim 1, wherein the dispersant is a calcium salt or a combination of the calcium salt with one or more selected from the group consisting of citrate, iron salt, zinc salt, magnesium salt, tranexamic acid, and 5-aminoketvaleric acid, and wherein the dispersant has a content of 1%-50 wt % based on a total weight of the polymer composite.

4. The polymer composite as a solid capable of being quickly dissolved or dispersed in an aqueous solvent according to claim 3, wherein the calcium salt is one or more selected from a group consisting of calcium lactate, calcium acetate, calcium chloride, and calcium hydrogen phosphate, and wherein the citrate is one or more selected from a group consisting of monosodium citrate, disodium citrate, and sodium citrate.

5. The polymer composite as a solid capable of being quickly dissolved or dispersed in an aqueous solvent according to claim 4, wherein the dispersant is a combination of the calcium chloride and the sodium citrate with a molar ratio of the calcium chloride to the sodium citrate of (0.1-99.9):1.

6. The polymer composite as a solid capable of being quickly dissolved or dispersed in an aqueous solvent according to claim 2, wherein the amphiphilic copolymer is a block copolymer having a hydrophilic block of at least one of poly(ethylene glycol) or a derivative thereof, and a hydrophobic block of polyester, and wherein the amphiphilic copolymer is at least one of a linear or branched n-block copolymer formed by covalently bonding a hydrophilic block and a hydrophobic block, where n is an integer of 2 to 10;

wherein the hydrophobic block of the amphiphilic copolymer has an average molecular weight of 500-2000, and the hydrophilic block of the amphiphilic copolymer has an average molecular weight of 500-3000;

wherein part or all of ends of the amphiphilic copolymer are connected with a functional group, and wherein:

the functional group is any one selected from a group consisting of hydrophilic hydroxyl, amino, carboxyl, imidazolyl, aldehyde group, cyano and nitro group, or the functional group is any one selected from a group consisting of hydrophobic alkyl group, sterol group, alkoxy group, aromatic group, arylheterocyclic group, amide ester group, halogen atom, trichloromethyl group, ester group and mercapto group; and wherein the polyester is one selected from a group consisting of poly(lactic acid), poly(lactic-co-glycolic acid), polycaprolactone, poly(caprolactone-co-glycolic acid), poly(lactic acid-co-caprolactone), polyvalerolactone, poly(lactic acid-co-valerolactone), polycarbonate, and poly(caprolactone-co-carbonate), or a combination thereof.

7. The polymer composite as a solid capable of being quickly dissolved or dispersed in an aqueous solvent according to claim 1, wherein the polymer composite is capable of being quickly dispersed in water or an aqueous solvent within 30 minutes by manual shaking.

8. A preparation method of the polymer composite as a solid capable of being quickly dissolved or dispersed in an aqueous solvent according to claim 1, comprising the following steps:

Step (1): compounding the dispersant and the polymer in a common solvent to provide a preliminary composite; and Step (2): drying the preliminary composite obtained in the step (1) to obtain the polymer composite.

9. The preparation method of the polymer composite as a solid capable of being quickly dissolved or dispersed in an aqueous solvent according to claim 8, wherein the drying in the step (2) is freeze drying.

10. The preparation method of the polymer composite as a solid capable of being quickly dissolved or dispersed in an aqueous solvent according to claim 8, wherein, in the step (1), a content of the dispersant in the common solvent is 0.5%-20 wt %, a content of the polymer in the common solvent is 1%-40 wt %, a compounding temperature is-10 to 50° C., a compounding time is 0.1-24 h, and a method for compounding is one selected from a group consisting of stirring, ultrasonication, shaking and standing, or a combination thereof.

11. The preparation method of the polymer composite as a solid capable of being quickly dissolved or dispersed in an aqueous solvent according to claim 9, wherein in the step (2)

for the freeze drying, a freezing temperature is −200 to −4° C., a freezing time is 0.1-24 h, and a drying time is 6-96 h.

* * * * *